(12) United States Patent
Petrovsky et al.

(10) Patent No.: US 7,821,269 B2
(45) Date of Patent: Oct. 26, 2010

(54) METHOD FOR DETERMINING THE DIELECTRIC CONSTANT OF PARTICLES

(76) Inventors: Vladimir Petrovsky, 903 Turkey Run, Rolla, MO (US) 65401; Fatih Dogan, 707 Oak Knoll Rd., Rolla, MO (US) 65401

( * ) Notice: Subject to any disclaimer, the term of this patent is extended or adjusted under 35 U.S.C. 154(b) by 325 days.

(21) Appl. No.: 12/135,169

(22) Filed: Jun. 7, 2008

(65) Prior Publication Data
US 2009/0261847 A1    Oct. 22, 2009

Related U.S. Application Data

(60) Provisional application No. 60/933,817, filed on Jun. 8, 2007.

(51) Int. Cl.
  *G01V 3/18* (2006.01)
  *G01R 27/26* (2006.01)
  *G01R 27/08* (2006.01)
(52) U.S. Cl. .................. 324/341; 324/663; 324/707
(58) Field of Classification Search ............... 324/707, 324/691, 649, 600, 601, 76.11, 71.1, 341, 324/663, 664, 689, 636
See application file for complete search history.

(56) References Cited

U.S. PATENT DOCUMENTS

| 5,451,882 | A  | * | 9/1995 | Wakino et al. | ............... 324/663 |
| 7,199,591 | B2 | * | 4/2007 | Ehata | ........................... 324/636 |
| 2007/0085552 | A1 | * | 4/2007 | Ehata | ........................... 324/636 |

* cited by examiner

*Primary Examiner*—Hoai-An D Nguyen
(74) *Attorney, Agent, or Firm*—C. John Brannon; Brannon & Sowers PC

(57) ABSTRACT

A method of measuring the dielectric constant of a powder, including selecting a powder having an unknown first dielectric constant, selecting a liquid having a known second dielectric constant, and introducing a predetermined amount of powder into a predetermined volume of liquid to define a slurry characterized by a known volume fraction of powder. Next, the impedance spectra of the slurry is plotted over a predetermined frequency range, the measured dielectric constant data is read and the appropriate equivalent circuit for the slurry is determined. Appropriate equivalent circuit equations are applied to the measured dielectric constant data and the first dielectric constant is calculated from the appropriate equivalent circuit equations, known volume fraction of powder and measured dielectric constant data.

20 Claims, 6 Drawing Sheets

METHOD FOR DETERMINING THE DIELECTRIC CONSTANT OF PARTICLES

CROSS-REFERENCE TO RELATED APPLICATIONS

This patent application claims priority to co-pending U.S. Provisional Patent Application Ser. No. 60/933,817 filed on Jun. 8, 2007.

GRANT STATEMENT

This invention technology was made with government support under Grant No. RG001083 from the National Science Foundation, as part of the Center for Dielectric Studies, and Grant No. N000-14-05-1-0541 from the Office of Naval Research. The Government has certain rights to this invention.

TECHNICAL FIELD

The invention relates generally to the field of electrical characterization of particulate materials, and, more particularly, to a method for determining the dielectric constant of ceramic and other particles in suspension.

BACKGROUND

Various dielectric materials used in capacitor industry can be considered as two-phase systems such as polymer capacitors filled with ceramic particles (3-1 composites). Even pure ceramic capacitors often behave as two-phase systems because of significant differences between the physical properties of the grain and the physical properties of the grain boundaries. Hence, to better understand the electrical properties of the overall system, the contributions of the individual phases should be distinguished. Regarding polymer-particle composites for electronic applications, although the dielectric properties of the polymeric phase can be measured simply using a bulk sample, it remains a challenging task to determine the dielectric properties of ceramic filler particles.

Various approaches have been used to estimate the dielectric constant of ceramic particles. One such approach arises from electrical characterization of sintered dense ceramic materials. This approach allows precise characterization of the sintered material, but cannot be used to estimate the dielectric properties of loose ceramic particles. For example, internal stresses within the polycrystalline sintered ceramics could unpredictably influence the local dielectric properties of the material, whereas loose particles in the form of powders are not mechanically constrained. Furthermore, the dielectric properties of particles in nanometer size scale may be significantly different than those in micrometer size scale. Although the dielectric properties of sintered ceramics as a function of grain size are widely studied, such investigations for particulate materials have been limited mainly due to the lack of reliable characterization methods to determine the permittivity of particulate materials.

Another approach to estimate the dielectric properties of particles is to conduct capacitance measurements on powder compacts or slurries (particles suspended in a liquid) as two-phase systems, followed by application of theoretical models based on mixing rules. In particular, the Lorentz-Lorenz equation allows estimating effective dielectric constant $\epsilon_{\mathit{eff}}$ of a two component composite composed of uniformly distributed spherical particles with dielectric constant $\epsilon_1$ and volume fraction $\chi_1$ in the host media with dielectric constant $\epsilon_2$:

$$\frac{\epsilon_{\mathit{eff}} - \epsilon_2}{\epsilon_{\mathit{eff}} + 2\epsilon_2} = x_1 \frac{\epsilon_1 - \epsilon_2}{\epsilon_1 + 2\epsilon_2}. \tag{1}$$

Unfortunately, powder compacts do not represent an ideal system for which the mathematical models such as Eq. (1) would be applicable. The effective dielectric constant of the compact is highly sensitive to particle-particle interaction, which can lead to errors in estimation of the permittivity of particles based on mixing rules.

Characterization of slurries may be a more suitable approach to evaluate the dielectric constant of particles. In slurries the particles are dispersed in a liquid so that the application of Lorentz-Lorenz equation (1) would be more reasonable. Using liquids with a high dielectric constant $\epsilon_2$ would result in more accurate estimation of $\epsilon_1$ for particles with high dielectric constant (>1000) such as ferroelectrics. However, availability of liquids with sufficiently high permittivity is limited ($\epsilon_2 \sim 70$ for propylene carbonate or other highly polarizable liquids) so that calculating the permittivity of particles from the effective dielectric constant of slurry may involve high margin of errors.

In several studies, dielectric measurements using slurries are conducted at high frequency (10-20 MHz range) to ensure low dielectric losses so that the effective medium theory [such as Lorentz-Lorenz equation (1)] would be applicable. However, the dielectric constant of the slurry $\epsilon_{\mathit{eff}}$ should be measured very precisely with an accuracy of several decimal points in order to be able to calculate the dielectric constant of particles $\epsilon_1$ with an acceptably small margin of error. Other factors affecting the reliability of measurements using slurries include size, shape, agglomeration, and sedimentation of the particles. Non-ideal slurries with respect to particle dispersion could lead to significant errors in the calculated value of the dielectric constant of particles $\epsilon_1$. Hence, the theoretical models have been modified by introducing various parameters based on, e.g., particle shape and size factors to minimize deviations of slurries from ideal systems. Lorentz-Lorenz equations or fine element models which are modified by incorporating such parameters are used to calculate the dielectric constant $\epsilon_1$ of particles. The effects of introducing multiple parameters and correction factors into a measurement technique already requiring high accuracy are to render the calculated dielectric constant values inherently suspect.

Thus, there remains a need for a technique or means for measuring the dielectric constant of insulative particles, such as ceramic, polymer, and/or biological particulate materials. The present invention addresses this need.

SUMMARY OF THE INVENTION

The present invention relates to a method of measuring the dielectric constant of particles, particularly ceramic particles.

One object of the present invention is to provide an improved method for measuring the dielectric constant of particulate materials. Related objects and advantages of the present invention will be apparent from the following description.

DESCRIPTION OF THE PREFERRED EMBODIMENTS

Figure 1:
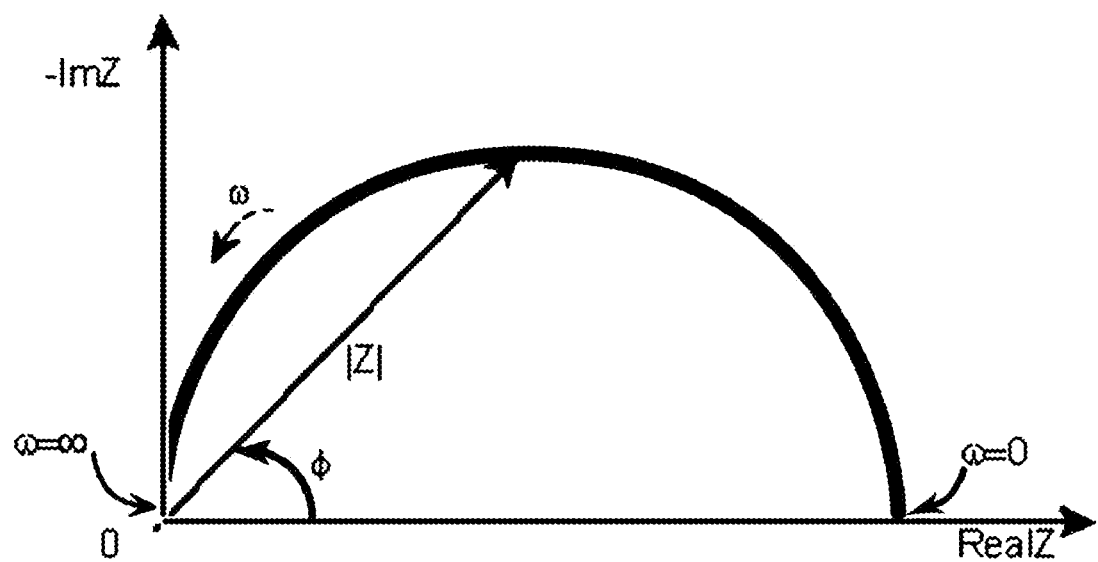
FIG. 1 is a diagrammatic illustration of a typical Nyquist plot.

For the purposes of promoting an understanding of the principles of the invention and presenting its currently understood best mode of operation, reference will now be made to the embodiments illustrated in the drawings and specific language will be used to describe the same. It will nevertheless be understood that no limitation of the scope of the invention is thereby intended, with such alterations and further modifications in the illustrated device and such further applications of the principles of the invention as illustrated therein being contemplated as would normally occur to one skilled in the art to which the invention relates.

Electrochemical Impedance Spectroscopy

Electrochemical impedance spectroscopy is a well established method for investigating electrical properties of materials, such as multiphase systems. As measured by EIS, impedance is the property of a material by which the flow of electrical current is resisted. While similar in concept to electrical resistance, impedance is a more general parameter and is more directly applicable to real world materials. Electrical resistance R is usually defined to be the ability of a circuit element to resist the flow of electrical current according to Ohm's law, which is stated below as $$R = \frac{E}{I}$$

and defines resistance in terms of the ratio between voltage E and current I. However, this relationship is limited to the case of an ideally behaving resistor. An ideal resistor is limited by several underlying assumptions, including following Ohm's Law at all current and voltage levels, R is independent of frequency, and the AC current and voltage signals though the resistor are always in phase with each other. However, real world circuit elements exhibit much more complex behavior and require a more complex parameter for adequate description.

Impedance is a more general circuit parameter that, like resistance, measures the ability of a circuit to resist the flow of electrical current. However, unlike resistance, impedance is not limited by the simplifying assumptions listed above. Electrochemical impedance is typically measured by applying a small AC potential to a system or electrochemical cell and measuring the current through the cell. For convenience, the AC potential is usually applied as a sinusoidal potential excitation. The response to the AC potential is an AC current signal, containing the excitation frequency and its harmonics. This current signal can be readily mathematically analyzed.

Electrochemical impedance is normally measured using a small excitation signal, such that the cell's response is pseudo-linear. A linear (or pseudo-linear) system is useful, as the current response to a sinusoidal potential will be a sinusoid at the same frequency but shifted in phase. The excitation signal, expressed as a function of time, has the form $$E(t) = E_0 \cos(\omega t)$$

E(t) is the potential at time t, $E_o$ is the amplitude of the signal, and w is the radial frequency. In a linear system, the response signal, $I_t$, is shifted in phase and has a different amplitude, $I_0$ and may be expressed as $$I(t) = I_0 \cos(\omega t - \phi)$$

An expression analogous to Ohm's Law allows the impedance Z of a system to be given as $$Z = \frac{E(t)}{I(t)} = \frac{E_0 \cos(\omega t)}{I_0 \cos(\omega t - \phi)} = Z_0 \frac{\cos(\omega t)}{\cos(\omega t - \phi)}$$

The impedance is therefore expressed in terms of a magnitude, $Z_0$, and a phase shift. Plotting the applied, and typically sinusoidal, signal on the X-axis of a graph and the sinusoidal response signal I(t) on the Y-axis, an oval generated. This oval is known as a Lissajous figure. By applying the Eulers relationship $$\exp(j\phi) = \cos \phi + j \sin \phi$$

it is possible to express the impedance as a complex function. The potential is described as $$E(t) = E_0 \exp(j\omega t)$$

and the current response may be given as $$I(t) = I_0 \exp(j\omega t - j\phi)$$

Impedance Z may then be represented as a complex number $$Z = \frac{E}{I} = Z_0 \exp(j\phi) = Z_0 (\cos\phi + j\sin\phi)$$

The expression for Z is composed of a real and an imaginary part. By plotting the real portion on the X axis and the imaginary portion on the Y axis of a chart, a Nyquist plot is generated (see FIG. 1). The y-axis is negative and that each point on the Nyquist plot is the system impedance at one particular frequency.

Figure 2:
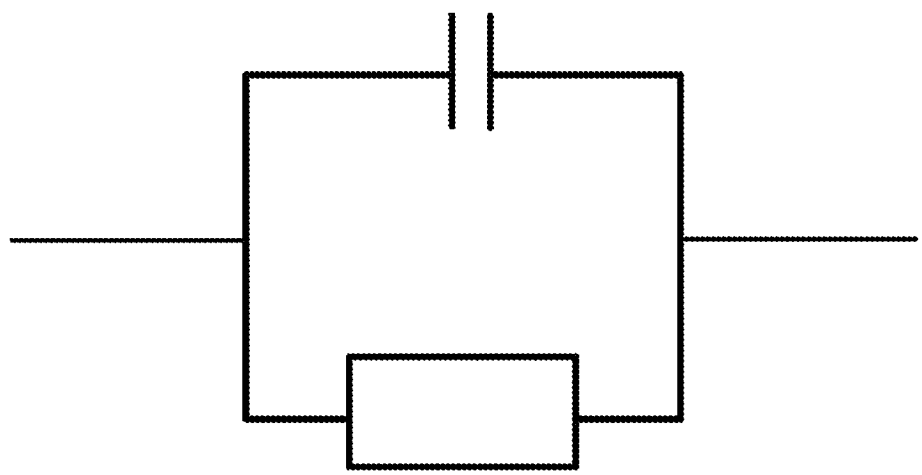
FIG. 2 is a schematic diagram of a simple RC equivalent circuit.

FIG. 1 is a sample generic Nyquist plot, with low frequency data on the right side of the plot and higher frequencies are on the left. On the Nyquist plot, impedance Z may be represented as a vector length, with the angle between the impedance vector and the x-axis being phase angle f. The Nyquist plot in FIG. 1 results from the equivalent electrical circuit of FIG. 2. The semicircle is characteristic of a single time constant; EIS plots may contain several time constants. Often only a portion of one or more of their semicircles is seen.

Dielectric Constant Measurement

According to the present novel technology, EIS may be adapted to reliably and accurately measure the dielectric constant of particles suspended in appropriate liquids. EIS techniques are applied to characterize slurries as two-phase systems, similar to the methods used to analyze polycrystalline materials, e.g., bulk and grain boundary conductivities. Theoretical models considering the parallel and series connections between each phase are two extreme cases to analyze the impedance spectra. In the case of parallel connection (see FIG. 3), the impedance spectra will consist of only one ideal semicircle with an effective dielectric constant of two phases $$\in_{\mathit{eff}} = \in_1 \chi_1 + \in_2 (1-\chi_1) \quad (2)$$

and the dielectric constant of the powder may be expressed as $$\in_1 = [\in_{\mathit{eff}} - \in_2 (1-\chi_1)]/\chi_1$$

Figure 3A:
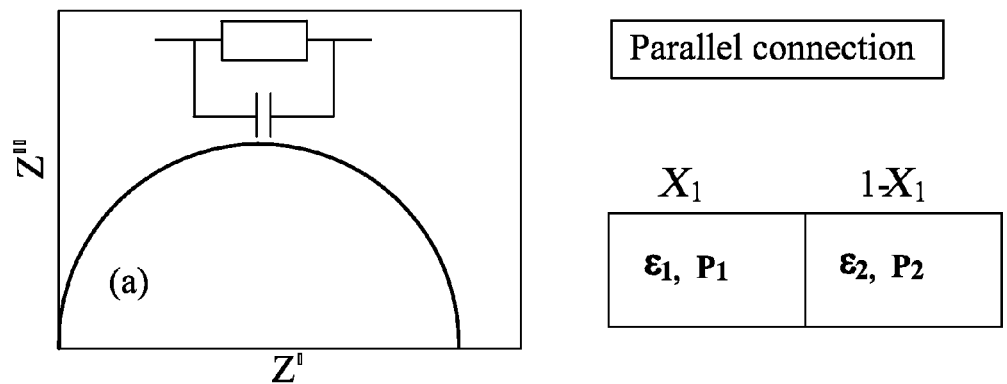
FIG. 3A is a schematic diagram of the impedance spectra for a two-phase system with elements connected in parallel.
Figure 3B:
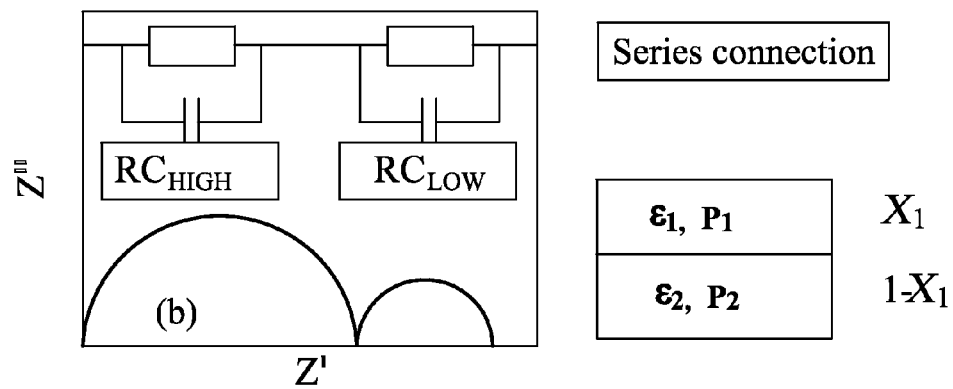
FIG. 3B is a schematic diagram of the impedance spectra for a two-phase system with elements connected in series.

If phases are connected in series, as shown in FIG. 3, the impedance spectra reveal two ideal semicircles. The effective dielectric constants defined by the first ($\in_H$ high frequency) and second ($\in_L$ low frequency) semicircles are expressed by $$\in_H = \in_2/(1-\chi_1) \quad (3)$$

$$\in_L = \in_1/\chi_1 \quad (4)$$

Thus, the dielectric constant of the powder is expressed as $$\in_1 = \in_L \chi_1$$

Semicircles in impedance spectra of slurries may overlap, since dispersion of particles in slurries is not ideal (or uniform). The effective dielectric constant retrieved from the high frequency semicircle would follow the Lorentz-Lorenz equation (1) or Eq. (3) depending on the slurry characteristics and particle volume fraction $\chi_1$. The low frequency semicircle is coupled with the dielectric constant of particles $\in_1$ in the slurry. The effective dielectric constant, retrieved from the low frequency semicircle, can be expected within a range from $\in_1$ to $\in_1/\chi_1$ (see Eq. 4).

Experimental Data

An electrochemical cell with aluminum electrodes (electrode diameter: 44 mm, distance between the electrodes: 1.1 mm) was built to conduct electrical measurements using slurries with different liquids and $SrTiO_3$ powders. An automated data acquisition system (1255b frequency response analyzer and 1470 cell tester) was used to collect data of the impedance spectra. Typically, at least one of the slurry components is conductive to obtain an impedance spectrum with distinctive semicircles. Since the conductivity of particles is effectively constant, liquids with proper conductivity are selected for use in the slurry preparation. It is helpful to choose liquids with ideal or close to ideal impedance spectra so that the analysis of the impedance spectra of slurries is simplified and the introduction of correction parameters for the measured data is unnecessary. Various liquids meet these requirements which allow dispersing of particles in nonaqueous slurries. Butoxyethanol was used in this study to prepare relatively stable slurries.

Figure 4:
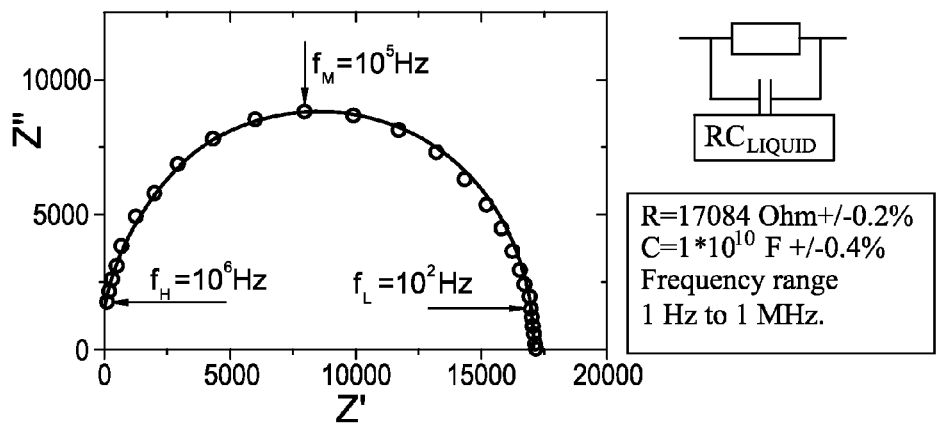
FIG. 4 is a schematic diagram of the impedance spectrum of butoxyethanol with an equivalent RC circuit according to one embodiment of the present novel technology.

The impedance spectra of butoxyethanol are depicted in FIG. 4. It is shown that single RC circuit allows a good fitting with experimental data in the frequency range from 100 Hz to 1 MHz (relative error for resistance is 0.2% and for capacitance is 0.4%). Using the capacitance value in FIG. 4 the dielectric constant of butoxyethanol was calculated to be 10.

Figure 5:
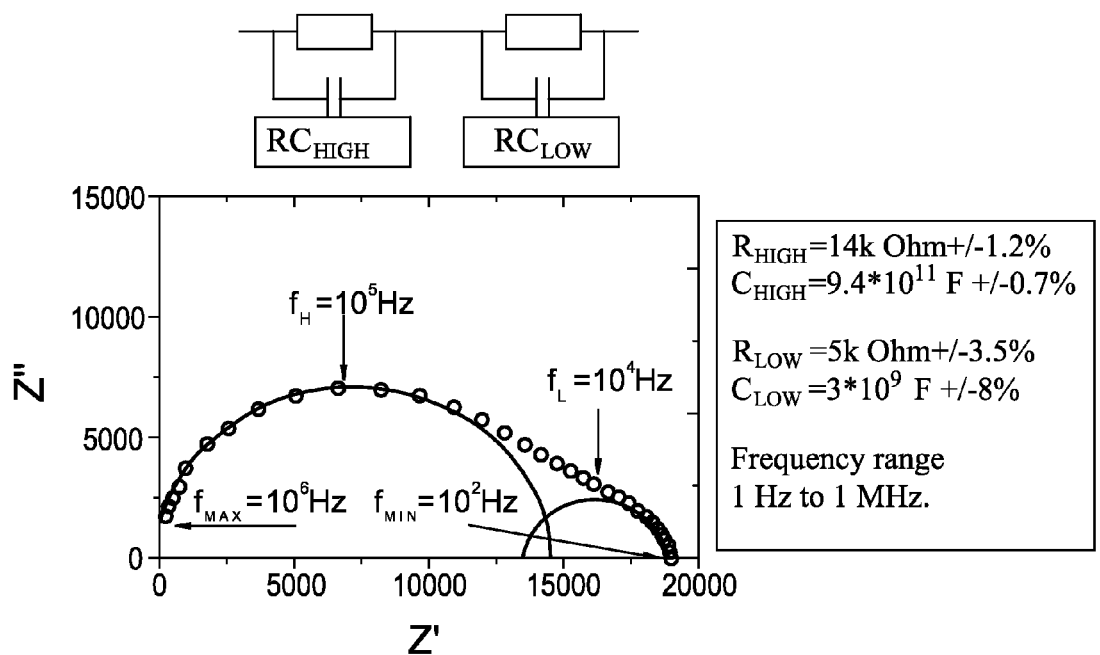
FIG. 5 is a schematic diagram of the impedance spectrum of a 5 volume percent $SrTiO_3$ in butoxyethanol slurry with an equivalent RC circuit measured according to the embodiment of FIG. 4.

Slurries with different solid loadings in the range from 5 to 35 volume percent were prepared by mixing $SrTiO_3$ powder with butoxyethanol for impedance spectroscopy measurements. Strontium titanate powder with particle size <5 μm was commercially acquired. FIG. 5 shows experimental data (open circles) and fitting results (two solid semicircles) for the slurry with 5 volume percent solid loading. Two distinct semicircles can be extracted from the spectra even at low solid loadings so that the model with two RC circuits connected in series ensures a good fitting (fitting errors are $\Delta R_{high}$=1.2%, $\Delta C_{high}$=0.7%, and $\Delta R_{low}$=3.5%, $\Delta C_{low}$=8% for high frequency and low frequency semicircles, respectively). The presence of additional semicircles, which may be related to other possible effects such as interfaces between particles and the liquid, was not observed using slurries investigated in this study.

The dielectric constant calculated from high frequency semicircle is equal to the dielectric constant of butoxyethanol, $\in_2$=10, within the margin of errors, so that there is no or minor influence of particles on impedance spectra at high frequency (at least for the slurry with 5 volume percent solid loading). On the other hand, the dielectric constant calculated from low frequency semicircle is equal to that of $SrTiO_3$, $\in_1$=300, within the margin of errors. Similarly there is substantially no or only minor influence of the liquid on the value of effective dielectric constant within the low frequency range. These results show that the permittivities of particles and the liquid phase in nonaqueous slurry can be extracted by impedance spectroscopy technique. Dielectric losses in the slurry are mostly connected with the conductivity of the liquid as dominating source of the losses for both high and low frequency semicircles.

As mentioned above regarding the prior techniques, determining the dielectric constant of particles by measurement of the effective dielectric constant of slurry and using effective medium models may result in significant differences of calculated values by several orders of magnitude. Minor variations of the solid loading in slurries or nonideal particle distribution can lead to significant errors in estimating the dielectric constant of particles. The present novel EIS techniques allow a reliable measurement of particle dielectric constant using slurries since different frequency ranges are selected to separate the contributions of the liquid and particles on impedance spectra.

Figure 6:
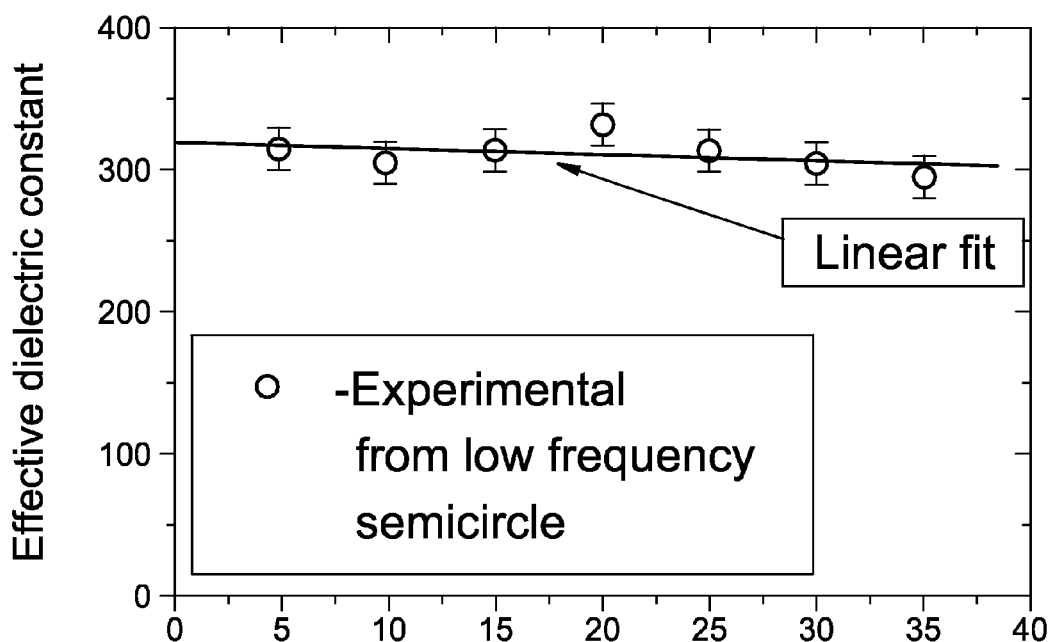
FIG. 6 is a graph of the calculated dielectric constant of $SrTiO_3$ particles as a function of increasing solid loading in butoxyethanol slurries according to the present novel technology.

FIG. 6 shows the dielectric constant of $SrTiO_3$ particles dispersed in butoxyethanol at different solid loadings. The dielectric constant values were calculated from low frequency semicircle of the impedance spectra in FIG. 5. It is revealed that these values remain nearly constant for solid loadings from about 5 to about 35 volume percent and equal to 309 (±3%). The measurements are quite insensitive to significant changes in the slurry such as solid loading or sedimentation of particles, so that the presented technique utilizing impedance spectroscopy offers a reliable and reproducible approach to measure the dielectric constant of particles.

Further investigation was conducted using metal oxide powders characterized by high dielectric constants (from 100 to 2000) and also using different liquids with dielectric constants in the range from 10 to 65. Standard powdered materials of $TiO_2$, $CaTiO_3$, $SrTiO_3$, and $BaTiO_3$ were obtained commercially. Samples were selected as being solid state synthesized powders with relatively big particle size (in the range 1 to 5 μm) so as to have dielectric constants in powdered materials as close as possible to the dielectric constants of the respective bulk materials for comparison and confirmation of the technique.

High purity organic solvents were selected as host liquids for slurry preparation. These included propylene carbonate 99.7% (dielectric constant 65), ethylene glycol 99.8% (dielectric constant 37), and Butoxyethanol >99% (dielectric constant 10). Slurries were prepared by mixing proper amounts of the powders with the host liquids and dispersed ultrasonically for 10 minutes by ultrasonic processor.

An electrochemical cell with stainless steel electrodes (electrode diameter 44 mm, distance between electrodes 1.1 mm) was used for electrical characterization of the slurries. Again, an automated system (1255b frequency response analyzer and 1470 cell tester) was used to collect data of the impedance spectra.

Figure 7:
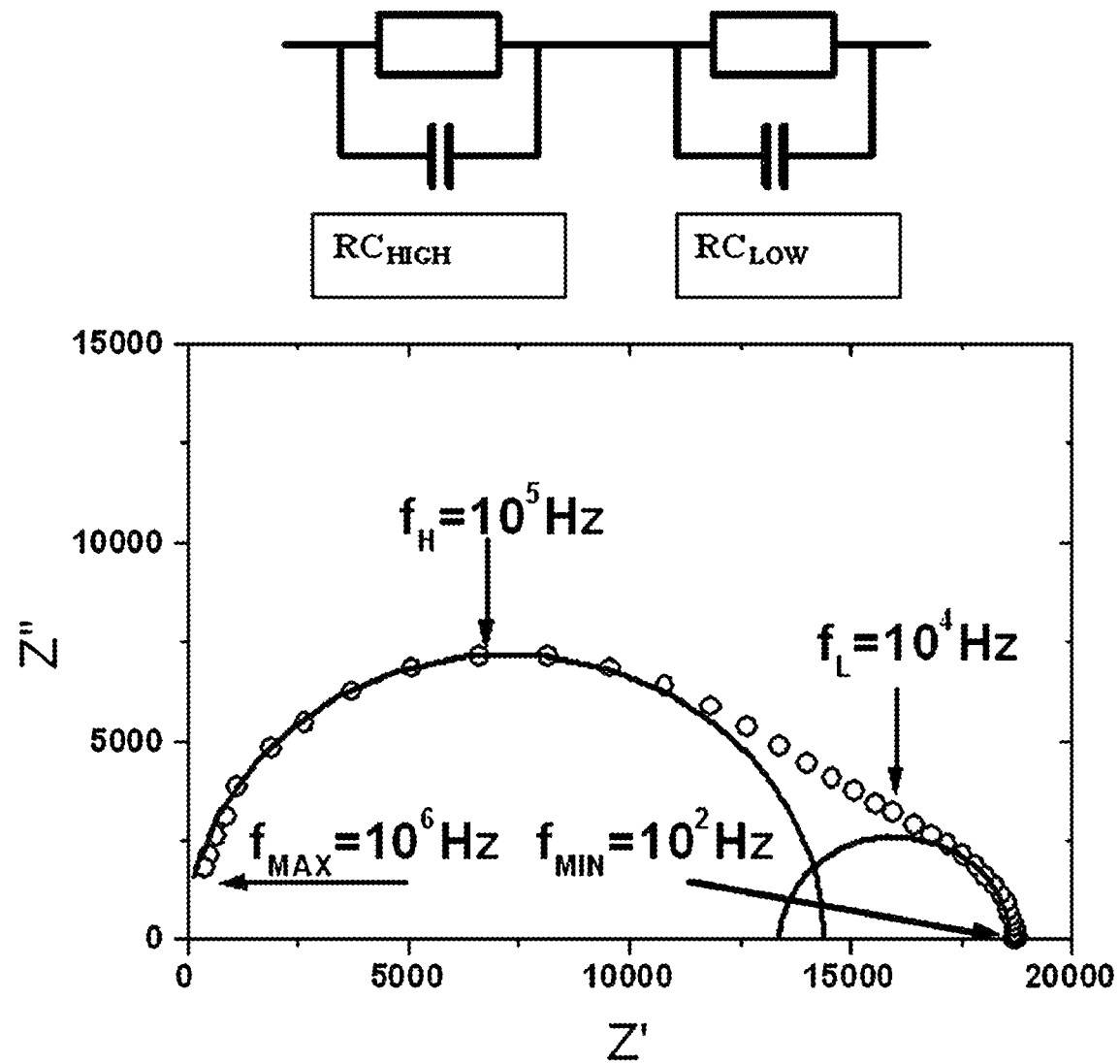
FIG. 7 is a sample impedance spectrum graph for use with the RC element equivalent circuit to determine the dielectric constant of an unknown powder according to the present novel technology.

Numerical parameters of the particulate material can not be obtained directly from the slurry impedance spectra. Physical modeling and mathematical fitting need to be applied to extract quantitative values such as powder dielectric constant from the slurry impedance spectra. As before, an equivalent circuit approach was used in our initial investigation for this purpose (see FIG. 7). It was determined that fitting the spectra by two RC elements connected in series allows acceptable accuracy of the fitting parameters with an error of less than 3%, so this approach was used for powder dielectric constant evaluation for all slurries investigated.

Figure 8:
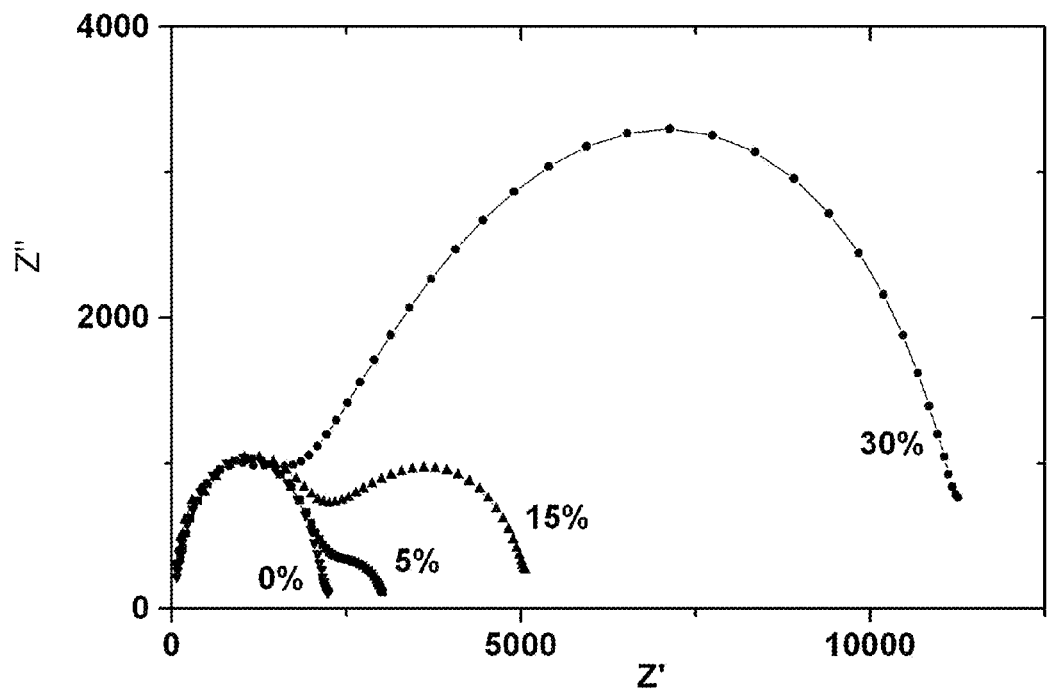
FIG. 8 is a graph of the impedance spectra of slurries with different $BaTiO_3$ powder loading.

As with the previous example, the impedance spectra contains only one semicircle for pure liquids connected with Maxwell relaxation process in conductive material. Electrical field relaxation in powder particles leads to additional relaxation process and, consequently, second semicircle emerges in the spectra which are illustrated in FIG. 8. FIG. 8 also shows changes in impedance spectra of Butoxyethanol, likely caused by addition of $BaTiO_3$ powder into the liquid from 0 up to about 30 volume percent. It can be seen that high frequency semicircle of the spectra shows only slight changes during addition of the powder. Vice versa, low frequency response of the impedance spectra increases proportionally to the powder addition.

Figure 9:
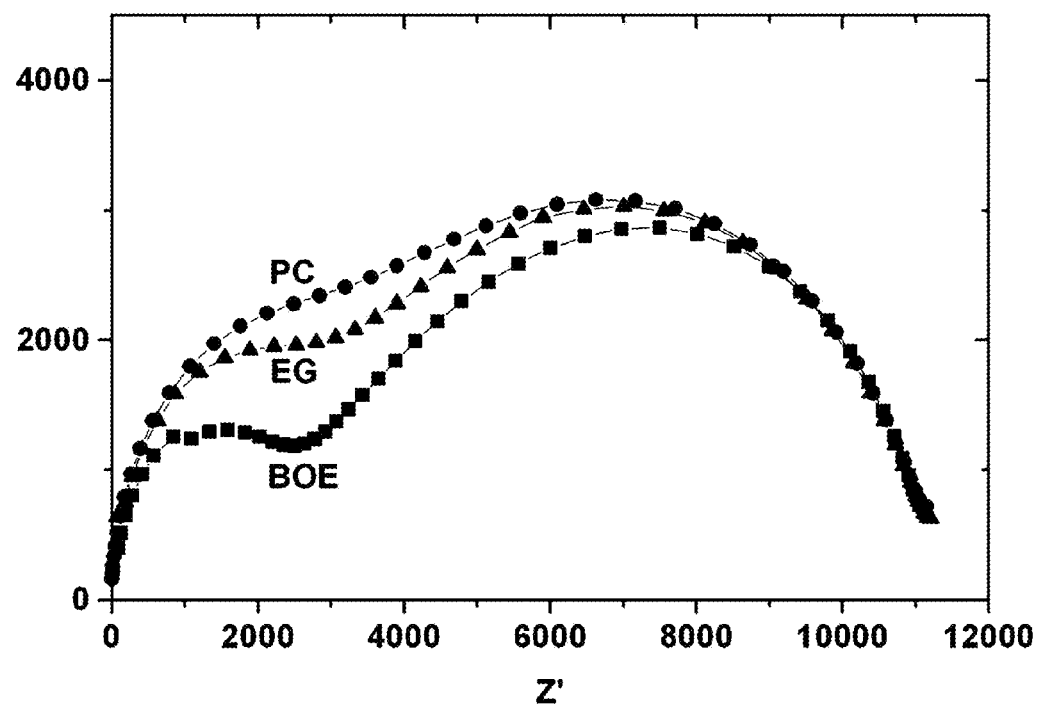
FIG. 9 is a graph of the impedance spectra of three slurries of different liquids (butoxyethanol, ethylene glycol, and propylene carbonate), each having 25 volume percent $BaTiO_3$ powder.

FIG. 9 illustrates a reverse situation. While the type and amount of the powder in the slurries are the same for all impedance spectra presented in the illustration (25 volume percent $BaTiO_3$ powder), host liquids (butoxyethanol, ethylene glycol and propylene carbonate) present slurry media characterized by differing dielectric constants of 10, 37 and 65, respectively. FIG. 9 clearly shows that properties of the host liquid influences the high frequency part of the spectra while low frequency response is substantially insensitive to the liquid properties.

Figure 10:
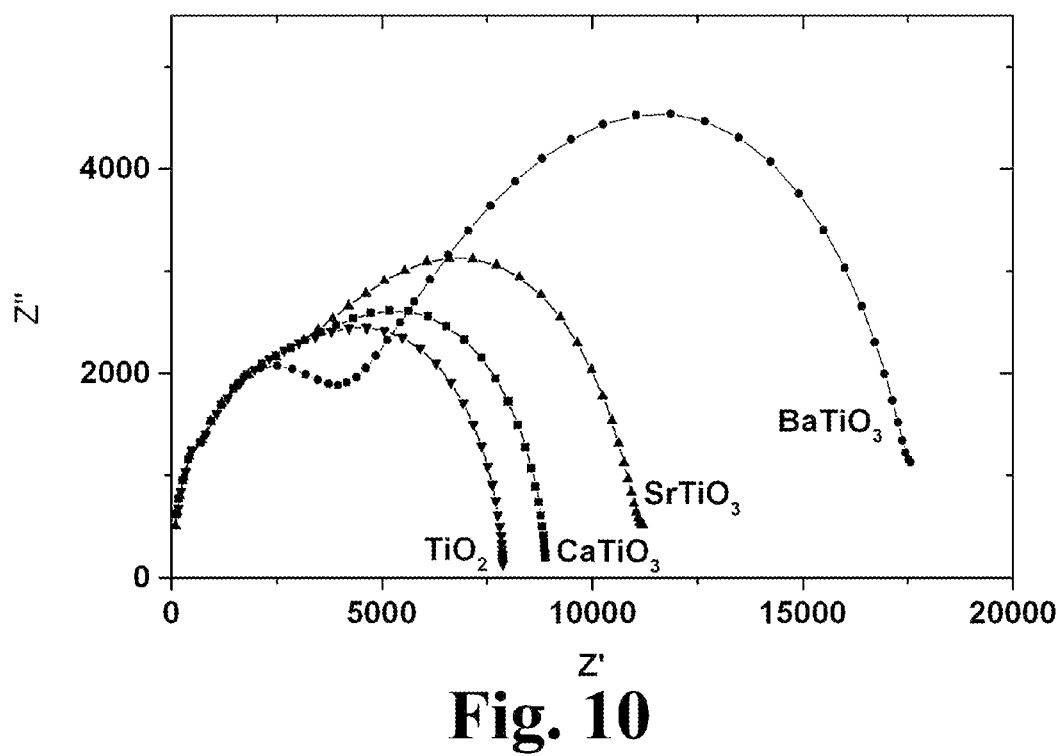
FIG. 10 is a graph of the impedance spectra of a plurality of butoxyethanol-based slurries, each containing 25 volume percent of a different powder (respectively, $TiO_2$, $CaTiO_3$, $SrTiO_3$, and $BaTiO_3$).

It is obvious that proper the high frequency part of the spectra should be used for extracting information concerning dielectric characterization parameters of the liquid component and the low frequency part of the spectra should contribute information regarding the dielectric characterization parameters of the powder components. This is clearly illustrated in FIG. 10, which illustrates the impedance spectra of Butoxyethanol based slurries containing the same amounts of different powders ($TiO_2$, $CaTiO_3$, $SrTiO_3$, and $BaTiO_3$). It can be seen from FIG. 10 that the high frequency part of the spectra is not substantially sensitive to the powder nature so all spectra are overlapped in this frequency range. At the same time, low frequency parts of the spectra are quite different for different powders.

Figure 11:
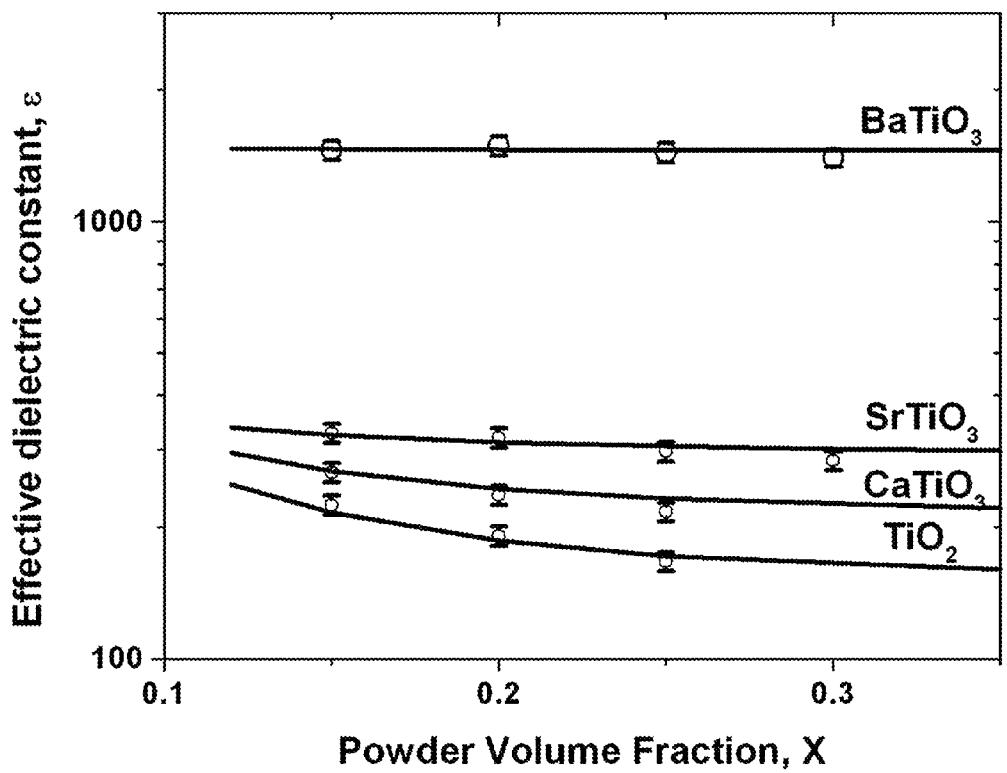
FIG. 11 is a graph of the powder volume fraction against the effective dielectric constant for butoxyethanol-based slurries of $TiO_2$, $CaTiO_3$, $SrTiO_3$, and $BaTiO_3$ powders.

The results of the investigation are summarized in FIG. 11. Effective dielectric constant for different powders plotted as a function of powder volume fractions in the slurries for all powders investigated. This dielectric constant was calculated from low frequency semicircle on impedance spectra using equivalent circuit with two RC elements connected in series. Butoxyethanol was used for slurries preparation in this particular case, but slurries prepared using other host liquids show very similar results. It can be seen from the figure that effective dielectric constant does not change much with the powder volume fraction for all materials investigated and has relatively high accuracy (error bars in the figure show an accuracy of 5%).

Measured values for powder dielectric constant were compared with the literature data for proper bulk materials (Table 1). It can be seen from the table that impedance spectroscopy allows accurately measuring dielectric constants for powdered materials and these values are in reasonable agreement with the values expected for these materials.

TABLE 1

| | Material | | | | |
|---|---|---|---|---|---|
| | $ZrO_2$ | $TiO_2$ | $CaTiO_3$ | $SrTiO_3$ | $BaTiO_3$ |
| Literature | 27-30 | 86-173 | 198 | 300-310 | 1200-3000 |
| Our results | 34 +/− 1 | 142 +/− 5 | 210 +/− 8 | 300 +/− 10 | 1400 +/− 50 |

Table 1. Comparison of literature values of dielectric constants measured on bulk materials with the values calculated from slurry impedance spectra for corresponding powders.

It is possible to conclude that impedance spectroscopy measurements are an efficient approach to electrical characterization of the powdered materials. EIS allows for determining dielectric constant of powdered dielectric materials by dispersing corresponding powders in the liquids (slurry preparation), measuring impedance spectra of the slurries and using equivalent circuit approach for extracting numerical parameters from the spectra.

The instant novel technology may be successfully used for characterization of powdered materials with wide range of dielectric constants (at least from several tens to several thousands) and has an accuracy of about 3%. Different host liquids can be used for the slurries preparation, so slurry properties can be optimized for particular range of powder dielectric constants, particle size, and the like.

In operation, the dielectric constant of a powder material may be measured by first selecting a powder having a powder dielectric constant desired to be measured and selecting a liquid having a known dielectric constant. A predetermined amount of powder is then introduced into a predetermined volume of liquid to define a slurry. The concentration or volume percent of the powder is known. Next, the impedance spectrum of the slurry is taken over a predetermined frequency range and plotted.

It should be noted that, for convenience, the electrical resistance of the liquid may be modified to shift the frequency response of the system to bring the frequency response of the liquid close to that of the suspended particles for ease of plotting. In other words, the resistance of the liquid is modified such that both plotted semicircles are within the frequency range of the spectrometer. Typically, the addition of small amounts of a modifier, such as acetic acid, is enough to increase the conductivity of the liquid enough to shift the frequency response of the system as desired. By selecting the appropriate equivalent circuit, the impedance spectrum is resolved into a high frequency response semicircle portion characteristic of the known dielectric constant of the liquid and a low frequency response portion characteristic of the powder dielectric constant. The high frequency response semicircle portion may then be calibrated (using the appropriate equivalent circuit equations) to the known dielectric constant of the liquid and the dielectric constant of the powder is likewise calculated.

The range of resistance of the system may be expressed according to Maxwell's equation $f=1/[(2\pi)(r)(k)(k_0)]$, where f is the frequency in Hz, r is the resistivity of the material in Ohm·cm, k is the relative permittivity of the material, and $k_0$ is the permittivity of vacuum ($8.85\ e^{-14}$ F/cm). The dielectric constant of the liquids used in the above examples ranges from about 10 to about 70. According to Maxwell's equation, resistivity and frequency are directly related. To close the semicircle, the range of frequencies should overlap around the Maxwell frequency f (i.e., the range should include a higher order and a lower order frequency). As a practical matter, the resistance range is defined by the impedance spectrometer available. Addition of a dielectric powder to the liquid introduces a second relaxation process, and thus the resistivity of the liquid is typically adjusted such that the frequency range necessitated by the powder and liquid suspension is within the range as defined by the impedance spectrometer.

While the dielectric constant of the measured powders is typically substantially higher than that of the liquid, the technique will also work if the dielectric constant of the powder is similar to or less than the liquid, providing the equivalent circuit is appropriately selected. Further, while the liquid is typically organic, any convenient fluid may be selected, including superfine powders that have fluid-like flow characteristics.

While the invention has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the invention are desired to be protected.

What is claimed is:

1. A method of measuring the dielectric constant of a loose powder, comprising in combination:
    a) selecting a powder having a powder dielectric constant desired to be measured;
    b) selecting a liquid having a known dielectric constant;
    c) introducing a predetermined amount of powder into a predetermined volume of liquid to define a slurry;
    d) plotting the impedance spectrum of the slurry over a predetermined frequency range;
    e) resolving the impedance spectrum into a high frequency response semicircle portion characteristic of the known dielectric constant of the liquid and a low frequency response portion characteristic of the powder dielectric constant;
    f) calibrating the high frequency response semicircle portion to the known dielectric constant of the liquid; and
    g) calculating the powder dielectric constant.

2. The method of claim 1 wherein the liquid has a dielectric constant between about 10 and about 70.

3. The method of claim 1 wherein the liquid is an organic solvent.

4. The method of claim 3 wherein the liquid is selected from the group including propylene carbonate, ethylene glycol, and butoxyethanol.

5. The method of claim 1 and further comprising:
    h) mixing the slurry to substantially evenly disperse the powder in the liquid.

6. The method of claim 1 wherein the powder is a metal oxide ceramic.

7. The method of claim 1 wherein step g) includes modeling the system as an equivalent circuit having two RC elements connected in series.

8. The method of claim 7 wherein the powder dielectric constant is expressed as the measured low frequency dielectric constant value multiplied by the volume fraction of powder dispersed in the slurry.

9. The method of claim 1 wherein the slurry has a powder volume fraction between about 0.05 and about 0.30.

10. A method of measuring the dielectric constant of a powder, comprising in combination:
    a) selecting a powder having an unknown first dielectric constant desired to be determined;
    b) selecting a liquid having a known second dielectric constant;
    c) introducing a predetermined amount of powder into a predetermined volume of liquid to define a slurry characterized by a known volume fraction of powder;
    d) adjusting the conductivity of the slurry to shift the frequency response of the system for ease of measurement;
    e) plotting the impedance spectra of the slurry over a predetermined frequency range;
    f) reading the measured dielectric constant data from the plotted impedance spectra;
    g) determining the appropriate equivalent circuit for the slurry;
    h) applying the appropriate equivalent circuit equations to the measured dielectric constant data; and
    i) calculating the first dielectric constant from the appropriate equivalent circuit equations, known volume fraction of powder and measured dielectric constant data.

11. The method of claim 10 wherein the appropriate equivalent circuit is defined by two RC elements connected in series.

12. The method of claim 10 wherein the first dielectric constant is expressed as the measured low frequency dielectric constant value multiplied by the volume fraction of powder dispersed in the slurry.

13. The method of claim 10 wherein the appropriate equivalent circuit is defined by two RC elements connected in parallel.

14. The method of claim 10 wherein the second dielectric constant is substantially less than the first dielectric constant.

15. The method of claim 10 wherein the second dielectric constant is substantially greater than the first dielectric constant.

16. The method of claim 10 wherein the first and second dielectric constants are similar.

17. The method of claim 10 wherein the powder is a metal oxide ceramic.

18. The method of claim 10 wherein the powder is a polymer material.

19. A method of determining the dielectric constant of a first powder material, comprising:
   a) selecting a first powder characterized by a first dielectric constant desired to be determined;
   b) selecting a fluid having a known second dielectric constant;
   c) mixing a predetermined amount of powder into a predetermined volume of fluid to define a mixture characterized by a known volume fraction of powder;
   d) plotting the impedance spectra of the mixture over a predetermined frequency range;
   e) reading the measured dielectric constant data from the plotted impedance spectra;
   f) determining the appropriate equivalent circuit for the mixture;
   g) applying the appropriate equivalent circuit equations to the measured dielectric constant data; and
   h) calculating the first dielectric constant from the appropriate equivalent circuit equations, known volume fraction of powder and measured dielectric constant data.

20. The method of claim 19 wherein the fluid is a fine powder.

* * * * *